(12) United States Patent
Gome et al.

(10) Patent No.: US 12,644,089 B2
(45) Date of Patent: Jun. 2, 2026

(54) BIOLOGICAL FLUIDIC SYSTEM

(71) Applicant: THE INTERDISCIPLINARY CENTER HERZLIYA PROJECTS LTD., Herzliya (IL)

(72) Inventors: Gilad Binyamin Gome, Tel Aviv (IL); Iddo Yehoshua Wald, Tel Aviv (IL); Andrey Grishko, Kiryat Ono (IL)

(73) Assignee: THE INTERDISCIPLINARY CENTER HERZLIYA PROJECTS LTD., Herzliya (IL)

( * ) Notice: Subject to any disclaimer, the term of this patent is extended or adjusted under 35 U.S.C. 154(b) by 939 days.

(21) Appl. No.: 17/294,467

(22) PCT Filed: Nov. 19, 2019

(86) PCT No.: PCT/IL2019/051264
§ 371 (c)(1),
(2) Date: May 17, 2021

(87) PCT Pub. No.: WO2020/105044
PCT Pub. Date: May 28, 2020

(65) Prior Publication Data
US 2022/0010259 A1 Jan. 13, 2022

(30) Foreign Application Priority Data
Nov. 19, 2018 (IL) .......................................... 263127

(51) Int. Cl.
*C12M 1/00* (2006.01)
*C12M 1/12* (2006.01)
*C12M 1/34* (2006.01)

(52) U.S. Cl.
CPC ............ *C12M 37/00* (2013.01); *C12M 23/26* (2013.01); *C12M 23/28* (2013.01); *C12M 23/34* (2013.01);
(Continued)

(58) Field of Classification Search
CPC ...... C12M 37/00; C12M 23/26; C12M 23/28; C12M 23/34; C12M 29/12; C12M 29/20;
(Continued)

(56) References Cited

U.S. PATENT DOCUMENTS

| | | | |
|---|---|---|---|
| 7,745,211 B2 | 6/2010 | Takayama et al. | |
| 2005/0084951 A1 | 4/2005 | Rouhani et al. | |

(Continued)

FOREIGN PATENT DOCUMENTS

| | | |
|---|---|---|
| CN | 101680013 A | 3/2010 |
| CN | 102112594 A | 6/2011 |

(Continued)

OTHER PUBLICATIONS

Kai, Eleanor, Tingrui Pan, and Babak Ziaie. "A robust low-cost PDMS peristaltic micropump with magnetic drive." Tech. Dig. Solid-State Sensor, Actuator and Microsystems Workshop (Hilton Headâ04)(Hilton Head Island, SC). 2004. (Year: 2004).*

(Continued)

*Primary Examiner* — Liban M Hassan
(74) *Attorney, Agent, or Firm* — Vorys, Sater, Seymour and Pease, LLP; Maryellen Feehery Hank

(57) ABSTRACT

Provided is a biological fluidic system that provides a high degree of sterilization by performing the biological processing in a closed system in which the fluid is contained in chambers that are isolated from the environment in a manner that does not permit ingress of contaminants.

16 Claims, 4 Drawing Sheets

(52) U.S. Cl.
CPC ............ *C12M 29/12* (2013.01); *C12M 29/20* (2013.01); *C12M 41/12* (2013.01); *C12M 41/36* (2013.01)

(58) Field of Classification Search
CPC ...... C12M 41/12; C12M 41/36; C12M 23/16; C12M 31/10; C12M 23/42; C12M 23/44; C12M 25/04; C12M 29/10; C12M 23/04; C12M 31/02; C12M 33/14; C12M 41/06; B01L 3/502761; B01L 2200/0684; B01L 2300/0681; B01L 2300/123; B01L 2400/0481; B01L 2400/0683; B01L 3/563; C12N 1/04
See application file for complete search history.

(56) References Cited

U.S. PATENT DOCUMENTS

| | | | |
|---|---|---|---|
| 2008/0151686 A1 | 6/2008 | Meadows et al. | |
| 2011/0212493 A1 | 9/2011 | Hirschel et al. | |
| 2014/0162363 A1 | 6/2014 | Castillo Fernandez | |
| 2014/0234954 A1 | 8/2014 | Lee et al. | |
| 2014/0356849 A1* | 12/2014 | Wikswo ............. | G01N 33/5005 |
| | | | 435/284.1 |
| 2016/0168521 A1 | 6/2016 | Mottahedeh | |
| 2016/0346780 A1* | 12/2016 | Bransky ............... | G02B 21/244 |
| 2017/0044483 A1 | 2/2017 | Faltin et al. | |
| 2018/0066220 A1 | 3/2018 | Nath et al. | |
| 2018/0237737 A1 | 8/2018 | Stobbe | |

FOREIGN PATENT DOCUMENTS

| | | | | |
|---|---|---|---|---|
| CN | 102161967 A | 8/2011 | | |
| CN | 103215185 A | 7/2013 | | |
| CN | 103667054 A | 3/2014 | | |
| CN | 104560711 A | 4/2015 | | |
| CN | 105536898 A | 5/2016 | | |
| CN | 106232799 A | 12/2016 | | |
| EP | 0263634 A2 * | 4/1998 | | |
| JP | H09-287571 A | 11/1997 | | |
| JP | H11-70167 A | 3/1999 | | |
| JP | 2006527093 A | 11/2006 | | |
| JP | 2009172858 A | 8/2009 | | |
| JP | 2010502405 A | 1/2010 | | |
| JP | 2017516473 A | 6/2017 | | |
| KR | 20070120361 A * | 12/2007 | ............ | C12M 21/02 |
| WO | WO-0005337 A1 * | 2/2000 | ............ | C12M 21/02 |
| WO | 2018013606 A1 | 1/2018 | | |

OTHER PUBLICATIONS

Liu, Jessica F., et al. "Microfluidic diafiltration-on-chip using an integrated magnetic peristaltic micropump." Lab on a Chip 17.22 (2017): 3796-3803. (Year: 2017).*

Saren, A., A. R. Smith, and K. Ullakko. "Integratable magnetic shape memory micropump for high-pressure, precision microfluidic applications." Microfluidics and Nanofluidics 22 (2018): 1-10. (Year: 2018).*

* cited by examiner

BIOLOGICAL FLUIDIC SYSTEM

TECHNOLOGICAL FIELD

The present disclosure concerns a biological fluidic system, in particular a cultivation system.

BACKGROUND

There are many known systems for performing biological assays and cultivating microorganisms, cell cultures or hard and soft tissues. Since many of these systems require some degree of sterilization, or some measures of protection when working with, they may be not widely accessible to a variety of populations, such as students. Thus, an improvement of the accessibility for such systems may facilitate the exposure of many populations to use and experience them.

GENERAL DESCRIPTION

The present disclosure concerns a biological fluidic system that provides a high degree of sterilization by performing the biological processing in a closed system in which the fluid is contained in chambers that are isolated from the environment in a manner that does not permit ingress of contaminants. The biological fluid, e.g. liquid or gas, is included or processed within a biological processing arrangement formed between two polymeric sheets, that are fixed to one another, e.g. by welding, to thereby define said processing arrangement. The processing arrangement may be in some embodiments used as a cultivating arrangement for the cultivation of living matter. Some non-limiting examples for 'living matter' are microorganisms, cells, tissues. The polymeric sheets, particularly where the system is intended for cultivation of living matter (e.g. microorganisms; cells of animal or plant origin), may be made of transparent or translucent polymeric material. Said arrangement includes one or more processing chambers for accommodating reaction liquids that comprise biological components and one or more ducts to permit liquid circulation within the arrangement. The biological arrangement is pliable and through selective pressure on various regions thereof, e.g. on regions of the one or more ducts, a fluid is driven to flow to thereby circulate through said arrangement.

It is to be noted that the term 'fluid' includes, but not limited to, liquids, gases and plasmas.

The processing arrangement may be stretchable and contractible in some degree allowing the flow of fluids and biological components therein by applying forces, e.g. lateral forces, on the processing arrangement. Application of lateral forces on the processing arrangement may stimulate the cultivation of cells or tissues, such as muscle tissues, tendons and more.

The biological processing that is carried out within said arrangement may include, but not limited to, cultivation of microorganism, cell cultures (of animal or plant cells), soft and hard tissues, biological assays such as Isothermal PCR, immunoassays, protein based assays, chemical assays, chromatography, or other chemical and biochemical assays.

In a first aspect of this disclosure, provided is a system for cultivation of living matter such as cells or microorganisms. The system comprising a cultivating arrangement formed between two polymeric sheets fixed to one another. The sheets may be made of a variety of polymeric materials, including single layer or multi-layer polymeric sheets. The polymer may, for example, be nylon including polyamide and/or polyethylene. The cultivating arrangement is formed with at least one chamber that is configured for cultivating microorganisms and at least one duct, each linking between two ports of the at least one chamber. The at least one duct has a flow-driving region that is configured for engagement with a fluid driving mechanism that, through a peristaltic action propels fluid flow through the duct between the two ports. The term "first port" will be used, for convenience, for one of the ports and "second port" for the other. The qualification of the ports as "first" or "second" has no hierarchal significance and are used only in order to streamline the description. The fluids can flow in both directions, namely from the first port to the second and vice versa. When referring to fluids, it should be interpreted to include any substance that has the capability to flow, such as liquids, solutions, gases, etc. The fluid driving mechanism may be controllable either in terms of speed of action, namely the rate of fluids it propels in a time unit or in terms of predetermined operation times. For example, the fluid driving mechanism may be set to operate at a predetermined cycles, e.g. once every 1 hour or several times a day at a predetermined intervals between operation times, each operation may last for a few seconds or minutes.

In some embodiments, the first port is located at one side of the chamber, e.g. an upper side, and the second port at another side, e.g. a lower side. A flow of liquids between the ports, e.g. between a lower second port to an upper first port, circulates the liquid in the processing chamber. In this embodiment, a flow from the second port to the first causes the circulation of liquids from a bottom portion of the chamber to a top portion thereof, while a flow from the first, top port to the second causes bubbling of air from the top portion of the chamber into the liquid.

In some embodiments, the system further includes an inlet duct linkning the at least one chamber that is configured for cultivating microorganisms to a medium reservoir. The medium reservoir includes growth medium suitable for the microorganisms that grow in the at least one chamber. The growth medium is driven either by a manual force application or by a medium driving mechanism that drives the growth medium from the medium reservoir towards the at least one chamber. The medium reservoir may be part of the cultivating arrangement or connectable thereto.

In some embodiments, the system further includes an outlet duct linking the at least one chamber that is configured for cultivating microorganisms to a discharge reservoir that is configured to receive discharged medium from the at least one chamber. The discharged medium is driven either by a manual force application or by a discharge driving mechanism that drives the discharged medium from the at least one chamber towards the discharge reservoir. The discharge reservoir may be part of the cultivating arrangement or connectable thereto.

The flow-driving region of the duct may be made to trace at least a section of a circle and may be generally circular. The fluid driving mechanism is configured as a peristaltic pump to peristaltically propel the liquid and to permit the bi-directionality of the circulation of the fluids.

In some embodiments, the driving mechanism comprises at least one engaging element configured to engage the flow-driving region and to propel fluid therethrough. The engagement element may be physically separated from the driving mechanism and being magnetically coupled to a driving motor to be driven thereby to propel the fluid.

The system may comprise a venting arrangement to permit gas exchange between the interior of the processing arrangement and the exterior environment. The venting arrangement may comprise at least one of a (i) filter for filtering particles in the introduced gas, such as a HEPA filter, paper or plastic made filter, activated carbon filter; and (ii) uni-directional valve that permits either the introduction of gas into the processing arrangement or the flow of excess gas from the processing arrangement into the environment.

In some embodiments, the venting arrangement is configured to permit gas exchange without passage of microorganism therethrough, for example by having a swan-necked shape.

The processing arrangement may have an introduction region configured to hold the cells such that they are separated from the processing chamber that contains the necessary biological components for cultivation. This separation assists to control the initiation time of the cultivation process. The separation may be carried out by a (i) swan-necked duct linking the microorganisms and the cultivation chamber that requires application of force on the polymeric sheets to drive the microorganisms into the chamber; (ii) sealing member that separates the microorganisms region and the cultivation chamber, the sealing member being rupturable or breakable to permit the introduction of the microorganisms into the chamber; or (iii) combination of a swan-necked duct and a sealing member. The processing arrangement may also comprise an inoculation port for introducing microorganisms into the chamber.

In some embodiments, the processing chamber comprises one or more regions in which opposite walls thereof are fixed to one another, e.g. laser welded, to prevent substantial expansion of the dimensions of the chamber, due to the elasticity of its walls, in the presence of liquid or the increase of the internal pressure (e.g. by gaseous products of the microorganisms).

The processing arrangement preferably may be disposable.

The system further comprising a base structure that comprises the driving mechanism and configured for association with the cultivating arrangement.

In some embodiments, the system comprising a temperature control unit that comprises at least one temperature sensor for sensing the temperature of the fluids in the processing arrangement, and specifically in the cultivation chamber. The sensed temperature may affect the operation of the temperature control unit to maintain a range of temperatures within the processing arrangement, or more specifically within the cultivation chamber. The temperature control unit maintains the range of temperatures within the cultivation between 25° C. and 100° C.

The system may further comprise at least one light source and at least one light sensor for sensing the light reflection from or light transmission through the fluid within the cultivation chamber. The light source may be selected from any one of a laser source of a LED light source.

The sensed data may be communicated by a communication module to an external unit for either storing or processing the data.

Another aspect of the present disclosure provides a cultivating arrangement formed between two polymeric sheets. The arrangement comprises (i) a cultivation chamber, (ii) a duct between two ports of the chamber to permit flow of fluid between the two ports through the duct, and (iii) a flow-driving region defined within the duct that is configured for engagement with a fluid driving mechanism to thereby propel fluid flow between the two ports.

Another aspect of the present disclosure provides a biological fluidic system comprising a fluid driving mechanism and a biological arrangement formed between two polymeric sheets. The arrangement comprises (i) at least one chamber, (ii) at least one duct to permit flow of fluid between two ports of a chamber and/or between two chambers, and (iii) a flow-driving region defined within the at least one duct that is configured for engagement with the fluid driving mechanism to thereby propel fluid flow between the two ports.

Yet another aspect of the present disclosure provides a cultivating arrangement formed between two polymeric sheets and having a pre-cultivating, storage compartment, for storing living matter, that is separated from a cultivation chamber by a rupturable or breakable sealing. The sealing may be broken or ruptured by an external force, e.g. a finger pressing or an actuation arrangement configured to rupture the sealing and drive the living matter into the cultivation chamber via an inoculation port, the cultivation chamber comprises nutrients suitable for allowing cultivation of the living matter.

In some embodiments, the cultivation arrangement may further comprise a duct between two ports of the chamber to permit flow of fluid between the two ports through the duct, and having a flow-driving region defined within the duct that is configured for engagement with a fluid driving mechanism to thereby propel fluid flow between the two ports.

Yet another aspect of the present disclosure makes use of the structure of the fluidic system described above for performing chemical reactions in a sterilized closed system.

Therefore, provided is a system for performing chemical reaction. The system comprising a reacting arrangement formed between two polymeric sheets fixed to one another. The reacting arrangement is formed with a first and second chambers, each configured for holding a chemical component, and at least one duct linking between the first and the second chambers.

In some embodiments, each of the first and second chambers may be linked to one or more additional chambers holding additional chemical components via linking ducts.

In some embodiments, the first and the second chambers are separated by rupturable or breakable sealing. The sealing may be broken or ruptured by an external force, e.g. a finger pressing or an actuation arrangement configured to rupture the sealing and drive the chemical components from one chamber to the other.

In some embodiments, the reacting arrangement comprises one or more uni-directional valves permitting the introduction or removal of gas to or from one of the chambers.

In some embodiments, the reacting arrangement comprising a flow-driving duct linking between two ports of one of the first and second chambers and comprises a flow-driving region that is configured for engagement with a fluid driving mechanism that, through a peristaltic action propels fluid flow through the duct between the two ports.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows separately the cultivation arrangement and the base structure of the macro-fluidic system; FIG. 1B shows the cultivation arrangement associated with the base structure, together with the engaging elements engaging the flow-driving region; FIG. 1C shows the working scheme of a stretching mechanism macro-fluidic system of the present disclosure.

FIG. 2A shows a two chambers structure of the system; FIG. 2B shows a three chambers structure of the system.

DETAILED DESCRIPTION OF EMBODIMENTS

Figure 1A:
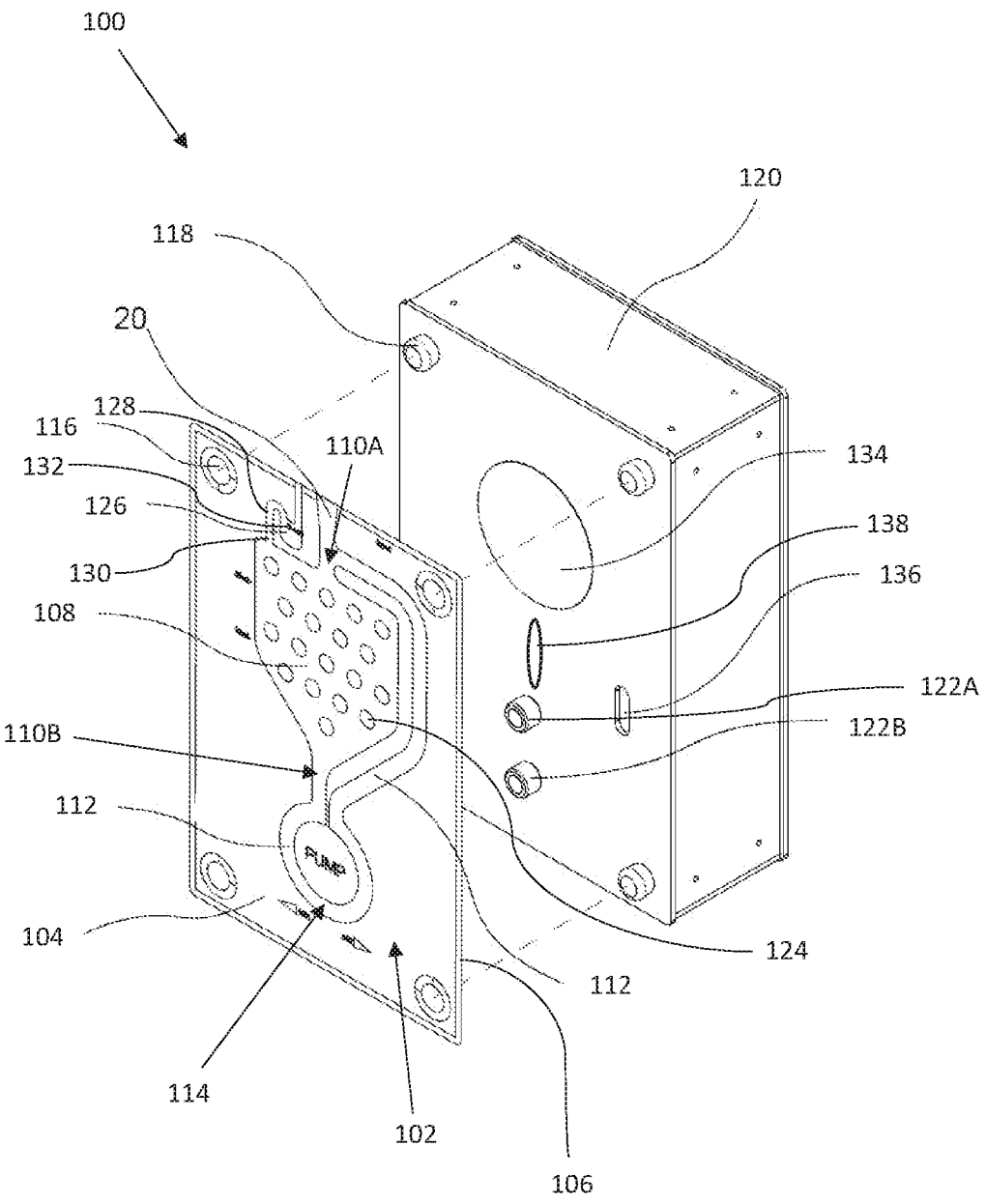
FIGS. 1A-1C are perspective views of schematic illustrations of examples of the macro-fluidic system of the present disclosure.

The present disclosure concerns a macro-fluidic system for performing biological processing such as microorganisms cultivation or a plurality of biological assays. FIG. 1A is a perspective view of a schematic illustration of the macro-fluidic system configured for cultivating microorganisms. The system 100 includes a cultivating arrangement 102 formed between two polymeric sheets 104 and 106 welded to one another by laser welding. The two sheets are welded to one another to form a structure of internal spaces confined between the two sheets that are not welded to one another. This spaces form, among other structures, a cultivation chamber 108 configured for accommodating microorganisms and biological components such as bacterial cells, growth media, antibiotics, viral particles, nucleic acids, enzymes, etc. to thereby serve as a basis for cultivation. The cultivation chamber 108 has two ports 110A and 110B, at a top and a bottom portion of the chamber 108 respectively. The two ports 110A and 110B are linked one to the other by a duct 112 that is configured to permit the flow of fluids therethrough, such as liquid and gases. The duct 112 has a generally circular region that is configured to serve as a flow-driving region 114.

The cultivation arrangement 102 comprises four through-holes 116 in its four corners to permit hanging of the cultivation arrangement 102 on four hanging members 118 on a base structure 120 for being in a close association therewith. The base structure 120 comprises a driving mechanism (not shown) that is configured to be coupled magnetically with engaging members 122A and 122B, which are detachable from the base structure. The engaging members 122A and 122B are configured to engage the flow-driving region 114 and driven by the driving mechanism, while the cultivation arrangement 102 and the base structure are associated, to thereby propel fluids within the cultivation arrangement 102. The cultivation chamber 108 includes a plurality of regions in which opposite walls thereof, namely the two polymeric sheets, are welded to one another. These welded regions 124 prevents swelling of the chamber 108 due to increase of pressure of the fluids therein and the elasticity/flexibility of the walls.

The cultivation chamber may be manufactured at first with the microorganisms separated from the cultivation chamber. The microorganisms may be stored in a microorganisms chamber 126 separated from the cultivation chamber 108 by a swan-necked region 128 linked to an inoculation port 130, and/or a rupturable or breakable sealing member 132 that upon rupturing or breaking thereof permits the introduction of the microorganisms into the chamber 108.

The base structure 120 is associated with a heat source 134 that is configured to be in a close association with the cultivation chamber 108 when the cultivation arrangement 102 and the base structure 120 are associated therewith. The heat source 134 is configured to maintain the cultivation chamber at a predetermined range of temperatures such as 32° C.-42° C. The heat source 134 may be in data communication with a temperature control (not shown) unit configured to control the operation of the heat source 134 to maintain the desired range of temperatures. The control unit may comprise one or more temperature sensors for sensing the ambient temperature and/or one or more temperatures of the cultivation arrangement, e.g. the cultivation chamber or the flow-driving region.

The base structure 120 formed with a slit 136, that upon association of the cultivation arrangement and the base structure, configured to face at least one of the duct 112 and the cultivation chamber 108. A spectrophotometer is comprised within the base structure 120 and configured to measure the spectral profile of the fluids within the cultivation arrangement 104 to obtain data indicative of microorganism growth or density. The spectrophotometer may be configured to illuminate with a wavelength in the range of 500-700 nm. In some embodiments, the spectrophotometer is configured to measure the fluid in the cultivation arrangement of at least 5 different wavelengths.

The base structure 120 may also comprise a light source configured to illuminate at least portions of the cultivation arrangement. The light source may illuminate through the slit 136 or an additional slit 138 with a wavelength in the range of 425-450 nm and/or 600-700 nm for the cultivation of photosynthetic cells.

Figure 1B:
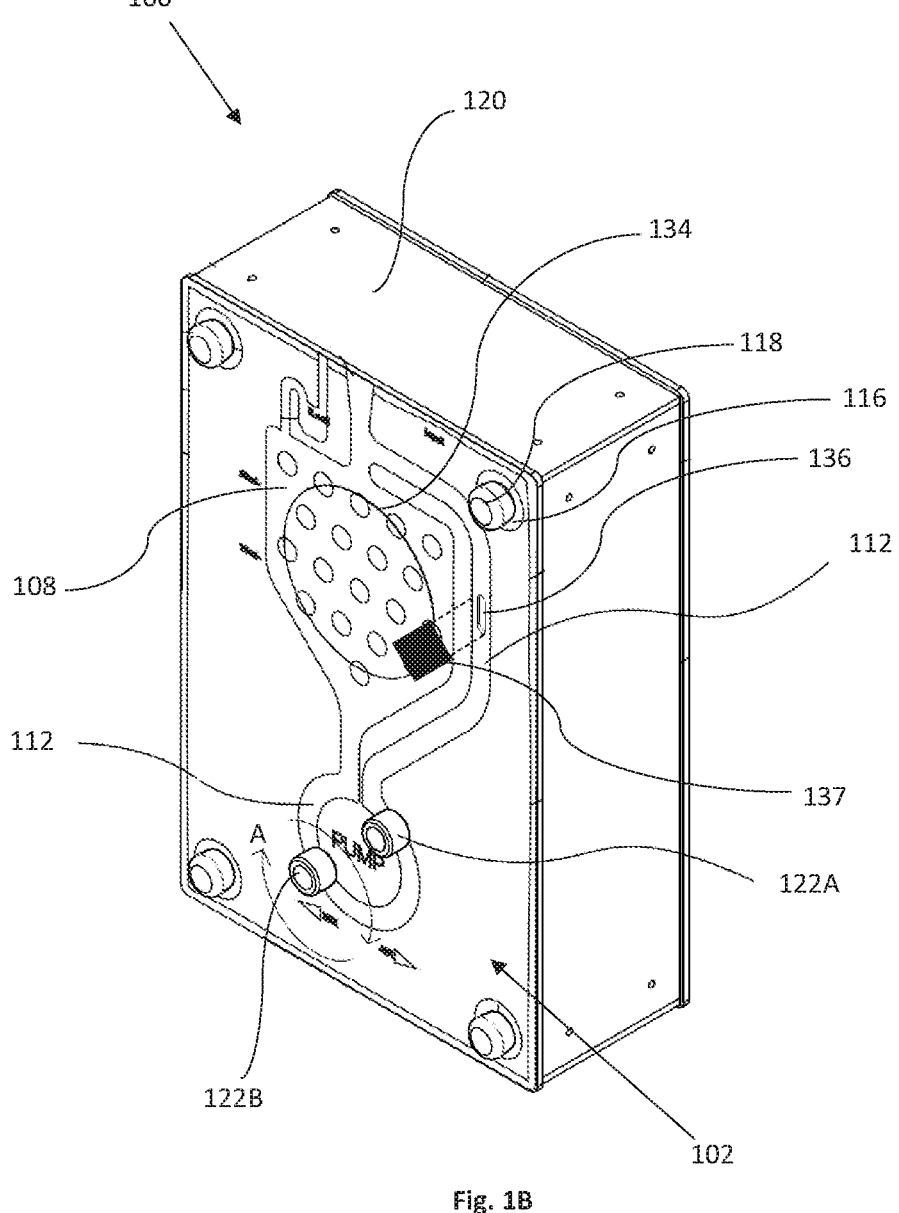

FIG. 1B exemplifies the system of the present disclosure, wherein the base structure 120 is associated with the cultivation arrangement 102 by the insertion of the hanging members 118 into the through-holes 116. In this example, the two engaging elements 122A and 122B are magnetically attracted to the driving mechanism, causing the attachment of the engaging elements to the flow-driving region 112. The engaging elements 122A and 122B are driven by the driving mechanism to rotate along the flow-driving region 112 in the direction of the arrow A, that causes a flow of gas from a top portion of the cultivation chamber 108 into a bottom portion thereof, and the bubbling of the gas into the liquid. When the driving mechanism drives the engaging elements in an opposite direction of the arrow A, liquid from a bottom portion of the cultivation chamber 108 flow through duct 112 to the top portion of the chamber 108. Therefore, the driving mechanism and the engagement elements 122A and 122B are configured together as a bi-directional peristaltic pump.

The heat source 134 is in thermal contact with the cultivation chamber 108 and configured to heat the chamber 108 to maintain a certain range of desired temperatures suitable for the biological processing, e.g. cultivation of cells.

The slit 136 faces the duct 112 to allow measurements of the spectrophotometer, or any other optical measurement device that may be accommodated within the base structure 120. A light isolating member 137 is configured to attach to the region of the slit 136 such that it is substantially isolating the measured portion of the duct 112 from ambient light while allowing the flow therein. The member 137 induces repetitive conditions between measurements, increasing the credibility of the measurements.

Figure 1C:
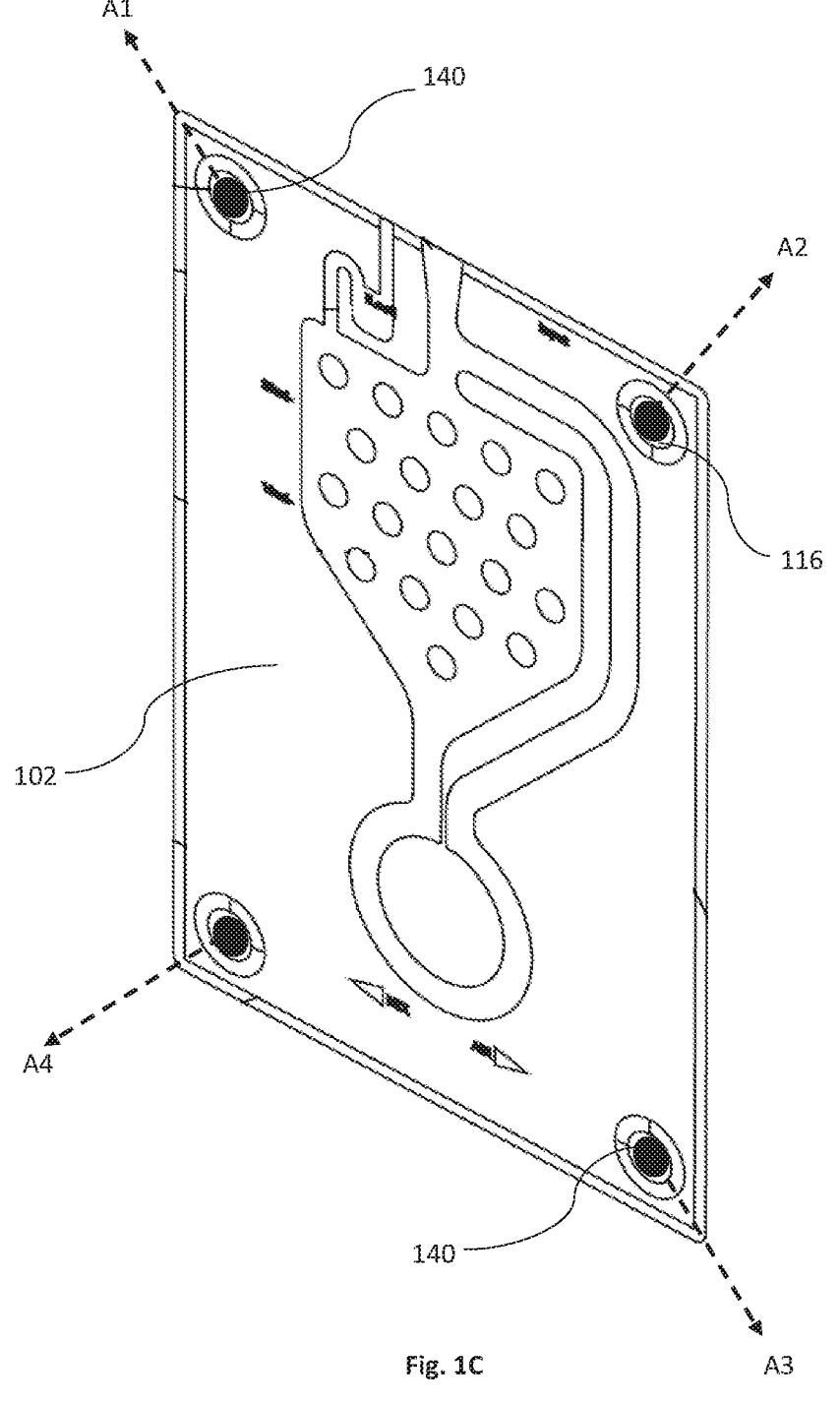

FIG. 1C is a schematic illustration of an example of an embodiment of the system of the present disclosure. Four members 140 of a stretching mechanism (not shown) are inserted into the through-holes 116 at the four corners of the cultivation arrangement 102, and configured to move in the direction of at least one of the arrows A1-A4 to apply forces on the cultivating arrangement 102 and stretch thereof, due to its pliable characteristics. This mechanism may enhance the cultivation of some types of cell cultures or tissues, such as muscle tissue or tendon.

Figure 2A:
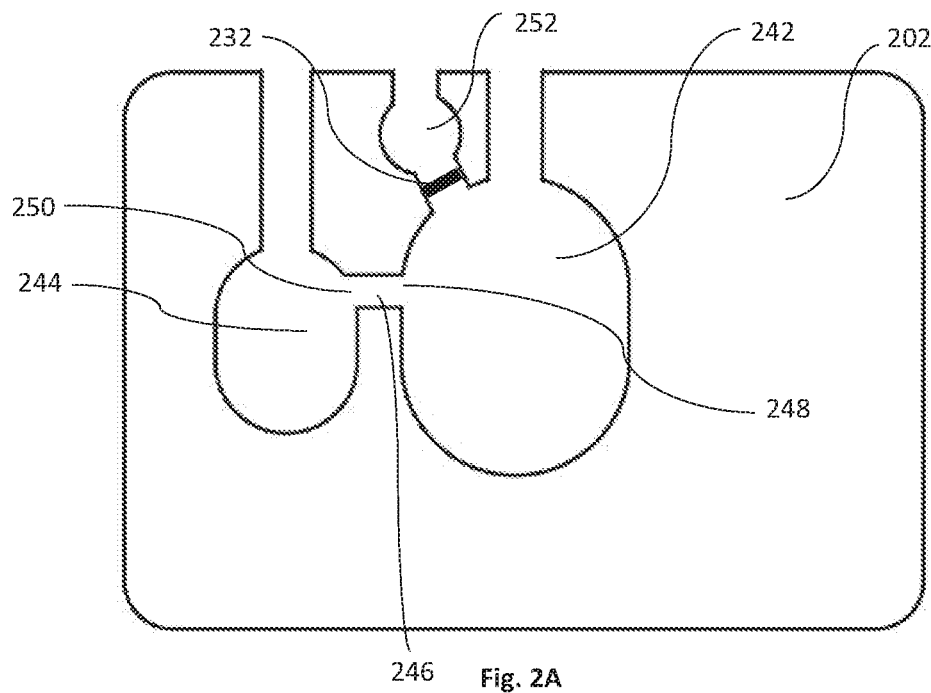
FIG. 2A-2B are top views of schematic illustrations of examples of the fluidic system of the present disclosure for carrying out chemical reactions.
Figure 2B:
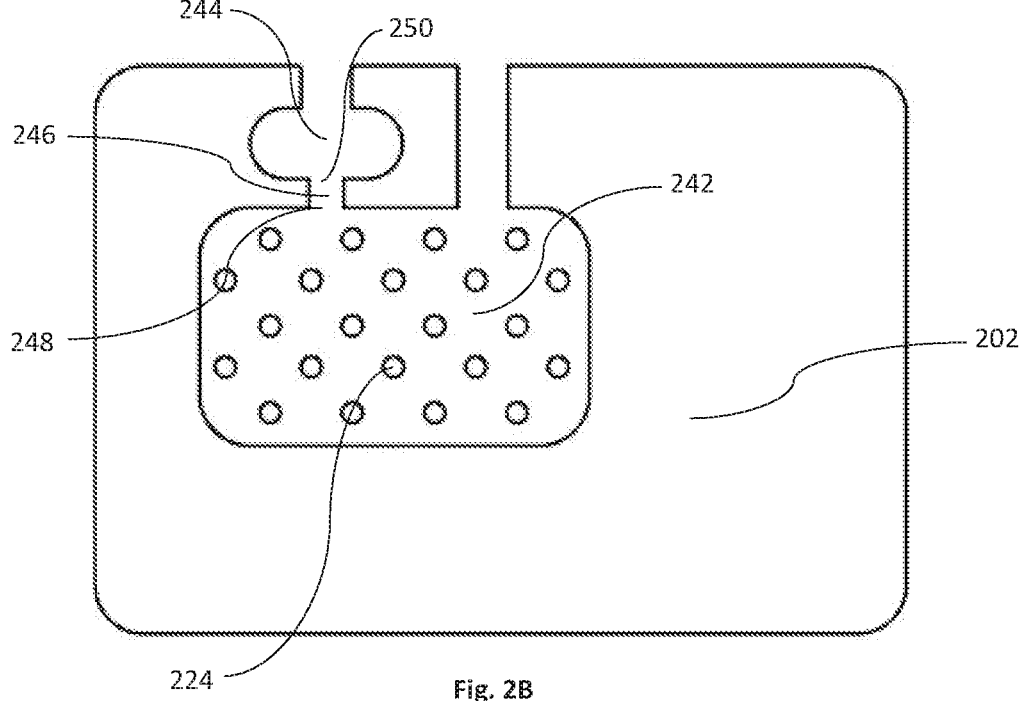

FIGS. 2A-2B are schematic illustrations of two embodiments a system for performing a chemical reaction according to the present disclosure. FIGS. 2A-2B show a reacting arrangement 202 formed between two polymeric sheets. The reacting arrangement 202 has a first and a second chamber 242 and 244, each comprises a chemical component. The chemical component may be a fluid, e.g. in a liquid or gas form or can be made of solid particles. A duct 246 links between ports 248, 250 of the first and second chambers 242 and 244 respectively.

In FIG. 2A chamber 242 is linked with an additional chamber 252 holding an additional chemical component. The introduction of the additional chemical component to the chamber 242 is prevented a rupturable sealing member 232 and upon rupturing thereof, the chemical component stored in chamber 252 is free to be introduced into chamber 242.

The invention claimed is:

1. A system for cultivating microorganisms or performing biological processing, comprising:
   a processing arrangement comprising:
   two pliable polymeric sheets oppositely disposed from each other forming first and second sides of the processing arrangement, the pliable polymeric sheets are fixed to one another at one or more portions of the respective sheets, and comprising:
      a processing chamber comprising:
         oppositely disposed ports;
         a cultivation chamber in communication with one of the ports; and
         a duct extending between the ports, along a pathway including a flow driving-region, to permit fluid flow between the two ports through the duct, and
      a base comprising:
      a fluid driving mechanism configured for operatively coupling with said processing arrangement, the fluid driving mechanism comprising:
         one or more magnetic engagement elements; and
         a driving motor magnetically coupled to said one or more magnetic engagement elements along the pathway including the flow-driving region on the second side of the processing arrangement, the driving motor configured to move the one or more magnetic engagement elements along a rotational pathway, the rotational pathway for alignment with the pathway including the flow driving-region of the duct;
      wherein, when the processing arrangement is operatively coupled to the base and the first side of the processing arrangement faces the base, each of the one or more magnetic engagement elements is positioned on the second side of the processing arrangement at one of a plurality of positions along the pathway including the flow-driving region to form a magnetic engagement with the driving motor, so that when the driving motor moves the one or more magnetic engagement elements along at least a portion of the pathway including the flow-driving region, each of said one or more magnetic engagement elements in the magnetic coupling applies pressure to the pathway including the flow-driving region, resulting in propelling the fluid in the pathway including the flow-driving region, and
      wherein, when said processing arrangement is not operatively coupled to the base, said one or more magnetic elements are adapted to be magnetically and removably attached to a surface of the base.

2. The system of claim 1, wherein the flow-driving region is circular and the fluid driving mechanism is configured to peristaltically propel the fluid.

3. The system of claim 1, comprising a venting arrangement permitting gas exchange between the interior of the processing arrangement and the exterior.

4. The system of claim 3, wherein the venting arrangement is configured to permit gas exchange without passage of microorganisms therethrough.

5. The system of claim 3, wherein the venting arrangement comprises a filter for filtering solid particles.

6. The system of claim 1, comprising an inoculation port for introducing living matter into the cultivation chamber.

7. The system of claim 1, wherein the oppositely disposed pliable polymeric sheets of the processing chamber are fixed to one another in one or more regions other than edges of the processing chamber.

8. The system of claim 1, wherein the processing arrangement is disposable.

9. The system of claim 1, wherein the two pliable polymeric sheets are welded to one another to form a structure of internal spaces confined between the two pliable polymeric sheets that are not welded to one another, defining the structure of said processing arrangement.

10. The system of claim 1, comprising a heat source operable for controllably heating the processing chamber and a temperature control unit, wherein the temperature control unit comprises at least one of a temperature sensor configured to sense a temperature in the processing arrangement, the temperature control unit is in data communication with the heat source and is configured to control its operation based on sensed temperature by the at least one of a temperature sensor to maintain a range of temperatures within the processing chamber.

11. The system of claim 1, wherein the base comprises: at least one light source configured to at least illuminate the processing chamber during the operative coupling of the base and the processing arrangement.

12. A biological fluidic system comprising:
   a biological arrangement comprising:
      two pliable polymeric sheets, that are oppositely disposed from each other to form first and second sides of the biological arrangement, the pliable polymeric sheets being fixed together at corresponding portions to one another:
      a plurality of processing chambers;
      oppositely disposed ports, at least one of the ports in communication with at least one of the plurality of processing chambers; and
      a duct extending between the ports, along a pathway including a flow-driving region, to permit fluid flow between the two ports through the duct, and
   a base structure comprising:
      a fluid driving mechanism configured for operatively coupling with said biological arrangement, the fluid driving mechanism comprising:
         one or more magnetic engagement elements; and
         a driving motor magnetically coupled to said to one or more magnetic engagement elements on the second side of the biological arrangement, the driving motor configured to the one or more magnetic engagement elements along a rotational pathway, the rotational pathway for alignment with the pathway including the flow-driving region of the duct;
      wherein, when the biological arrangement is operatively coupled to the base structure and the first side of the biological arrangement faces the base structure, each of the one or more magnetic engagement elements positioned on the second side of the biological arrangement at one of a plurality of positions along the pathway including the flow-driving region to form a magnetic engagement with the driving motor, so that when the driving motor moves the one or more magnetic engagement elements along the pathway including the flow-driving region, said one or more magnetic engagement elements in the magnetic applies pressure to the pathway including the flow-driving region, resulting in propelling the fluid in the pathway including the flow-driving region, and wherein, when said processing arrangement is not operatively coupled to the base, said one or more magnetic elements are adapted to be magnetically and removably attached to a surface of the base.

13. The system of claim 1, wherein the rotational pathway includes a clockwise or a counterclockwise pathway.

14. The system of claim 12, wherein the rotational pathway includes a clockwise or a counterclockwise pathway.

15. The system of claim 1, wherein the processing arrangement and the base are oriented vertically with respect to each other.

16. The biological fluid system of claim 12, wherein the biological arrangement and the base structure are oriented vertically with respect to each other.

\* \* \* \* \*